(12) United States Patent
Van Den Broeck et al.

(10) Patent No.: US 6,306,635 B1
(45) Date of Patent: Oct. 23, 2001

(54) FUNGAL CELLULASES

(75) Inventors: Henriëtte C. Van Den Broeck, Ede; Leendert H. De Graaff, Oosterbeek; Jacob Visser, Wageningen; Albert J. J. Van Ooijen, Voorburg, all of (NL)

(73) Assignee: Gist-Brocades B.V., Delft (NL)

( * ) Notice: Subject to any disclaimer, the term of this patent is extended or adjusted under 35 U.S.C. 154(b) by 0 days.

(21) Appl. No.: 09/478,816

(22) Filed: Jan. 7, 2000

Related U.S. Application Data

(62) Division of application No. 08/849,751, filed on Jun. 12, 1997, now Pat. No. 6,190,890.

(30) Foreign Application Priority Data

Oct. 13, 1995 (EP) .................................. 95202776

(51) Int. Cl.⁷ .............................. C12N 9/42; C12N 15/56
(52) U.S. Cl. ................. 435/209; 435/252.3; 435/254.1; 435/255.1; 536/23.2
(58) Field of Search .............................. 435/252.3, 255.1, 435/254.1, 209; 536/23.2

(56) References Cited

U.S. PATENT DOCUMENTS 5,475,101 * 12/1995 Ward et al. ............................ 536/23

FOREIGN PATENT DOCUMENTS

| 420 358 | 9/1990 | (EP) . |
| 96/29415 | 9/1996 | (WO) . |

OTHER PUBLICATIONS

Kelly et al. (1985) "Transformation of *Aspergillus niger* by the amdS gene of *Aspergillus nidulans*," *EMBO J.* 4:475–479.

Sakamoto et al. (1995) "Cloning and sequencing of cellulase DNA from *Aspergillus Kawachii* and its expression in *Saccharomyces Cerevisiae*," *Curr. Genet* 27:435–439.

Somogyi (1952) "Notes on Sugar Determination," *J. Biol Chem.* 195:19–23.

Tilburn et al. (1983). "Transformation by integration in *Aspergillus nidulans*, " *Gene* 26:205–221.

\* cited by examiner

*Primary Examiner*—Charles L. Patterson, Jr.
(74) *Attorney, Agent, or Firm*—Morrison & Forester LLP

(57) ABSTRACT

The present invention provides polypeptides with cellulase activity, corresponding DNA sequences, vectors, transformed hosts and a method for the production of these polypeptides, which are obtainable from *Aspergillus niger var. niger* or *Aspergillus niger var. tubigensis*.

16 Claims, 2 Drawing Sheets

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1017 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Aspergillus niger
      (B) STRAIN: N400
      (C) INDIVIDUAL ISOLATE: CBS120.49

(ix) FEATURE:
      (A) NAME/KEY: Coding Sequence
      (B) LOCATION: 57...773
      (D) OTHER INFORMATION: product="Cellulase"

(xi) SEQUENCE DESCRIPTION: SEQ ID NO:1:

GAATTCGGCA CGAGCGAATT TCCCTTGATT GCCGCTCCTC CGCTCTAACG CCCAAC ATG    59
                                                                           Met

```
AAG CTC CCC GTG TCA CTT GCT ATG CTT GCG GCC ACC GCC ATG GGC CAG        107
Lys Leu Pro Val Ser Leu Ala Met Leu Ala Ala Thr Ala Met Gly Gln
              5              10                 15

ACG ATG TGC TCT CAA TAT GAC AGT GCC TCG AGC CCC CGT TAT TCA GTG        155
Thr Met Cys Ser Gln Tyr Asp Ser Ala Ser Ser Pro Pro Tyr Ser Val
          20              25              30

AAC CAG AAC CTC TGG GGC GAG TAC CAA GGC ACC GGC AGC CAG TGT GTA        203
Asn Gln Asn Leu Trp Gly Glu Tyr Gln Gly Thr Gly Ser Gln Cys Val
      35              40              45

TAT GTC GAC AAA CTC TCC AGC AGT GGT GCA TCC TGG CAC ACC GAA TGG        251
Tyr Val Asp Lys Leu Ser Ser Ser Gly Ala Ser Trp His Thr Glu Trp
50              55              60              65

ACC TGG AGC GGT GGT GAG GGA ACA GTG AAA AGC TAC TCT AAC TCT GGC        299
Thr Trp Ser Gly Gly Glu Gly Thr Val Lys Ser Tyr Ser Asn Ser Gly
                70              75              80

GTT ACA TTT AAC AAG AAG CTC GTG AGT GAT GTA TCA AGC ATC CCC ACC        347
Val Thr Phe Asn Lys Lys Leu Val Ser Asp Val Ser Ser Ile Pro Thr
             85              90              95

TCG GTG GAA TGG AAG CAG GAC AAC ACC AAC GTC AAC GCC GAT GTC GCG        395
Ser Val Glu Trp Lys Gln Asp Asn Thr Asn Val Asn Ala Asp Val Ala
           100             105             110

TAT GAT CTT TTC ACC GCG GCG AAT GTG GAC CAT GCC ACT TCT AGC GGC        443
Tyr Asp Leu Phe Thr Ala Ala Asn Val Asp His Ala Thr Ser Ser Gly
       115             120             125

GAC TAT GAA CTG ATG ATT TGG CTT GCC CGC TAC GGC AAC ATC CAG CCC        491
Asp Tyr Glu Leu Met Ile Trp Leu Ala Arg Tyr Gly Asn Ile Gln Pro
130             135             140             145

ATT GGC AAG CAA ATT GCC ACG GCC ACA GTG GGA GGC AAG TCC TGG GAG        539
Ile Gly Lys Gln Ile Ala Thr Ala Thr Val Gly Gly Lys Ser Trp Glu
                150             155             160

GTG TGG TAT GGC AGC ACC ACC CAG GCC GGT GCG GAG CAG AGG ACA TAC        587
Val Trp Tyr Gly Ser Thr Thr Gln Ala Gly Ala Glu Gln Arg Thr Tyr
            165             170             175

AGC TTC GTG TCA GAA AGC CCT ATC AAC TCA TAC AGT GGG GAC ATC AAT        635
Ser Phe Val Ser Glu Ser Pro Ile Asn Ser Tyr Ser Gly Asp Ile Asn
        180             185             190

GCA TTT TTC AGC TAT CTC ACT CAG AAC CAA GGC TTT CCC GCC AGC TCT        683
Ala Phe Phe Ser Tyr Leu Thr Gln Asn Gln Gly Phe Pro Ala Ser Ser
    195             200             205

CAG TAC TTG ATC AAT CTG CAG TTT GGA ACT GAG GCG TTC ACC GGG GGC        731
Gln Tyr Leu Ile Asn Leu Gln Phe Gly Thr Glu Ala Phe Thr Gly Gly
210             215             220             225

CCG GCA ACC TTC ACG GTT GAC AAC TGG ACC GCC AGT GTC AAC TAGGGTTCT     782
Pro Ala Thr Phe Thr Val Asp Asn Trp Thr Ala Ser Val Asn
                230             235

AGAAGTAGCC TTTGAGGCAG AATCTGGGTA AATTGACTCC AGCTCGGGAG AATGATAGCT      842

TGTTTCTTCG TTCTGGAACG TTGGGCGTGT GAGAGCTAAA AAGTCGTACC CACTCTGATT      902

GGAAAGACTT ATTCAACATT GGTCCTTCCC TTCTGTTGGG CAAGGCATAG TTAGTGATTA      962

GACAAGTCAA GGTCATGGTG GATCCCTTGT AAAAAAAAAA AAAAAAAAAC TCGAG          1017
```

(2) INFORMATION FOR SEQ ID NO:2:

(i) SEQUENCE CHARACTERISTICS:
        (A) LENGTH: 239 amino acids
        (B) TYPE: amino acid
        (C) STRANDEDNESS: single
        (D) TOPOLOGY: linear -continued (ii) MOLECULE TYPE: protein (v) FRAGMENT TYPE: internal (xi) SEQUENCE DESCRIPTION: SEQ ID NO:2:

```
Met Lys Leu Pro Val Ser Leu Ala Met Leu Ala Ala Thr Ala Met Gly
 1               5                  10                  15

Gln Thr Met Cys Ser Gln Tyr Asp Ser Ala Ser Pro Pro Tyr Ser
            20                  25                  30

Val Asn Gln Asn Leu Trp Gly Glu Tyr Gln Gly Thr Gly Ser Gln Cys
            35                  40                  45

Val Tyr Val Asp Lys Leu Ser Ser Ser Gly Ala Ser Trp His Thr Glu
 50                  55                  60

Trp Thr Trp Ser Gly Gly Glu Gly Thr Val Lys Ser Tyr Ser Asn Ser
 65                  70                  75                  80

Gly Val Thr Phe Asn Lys Lys Leu Val Ser Asp Val Ser Ser Ile Pro
                85                  90                  95

Thr Ser Val Glu Trp Lys Gln Asp Asn Thr Asn Val Asn Ala Asp Val
                100                 105                 110

Ala Tyr Asp Leu Phe Thr Ala Ala Asn Val Asp His Ala Thr Ser Ser
                115                 120                 125

Gly Asp Tyr Glu Leu Met Ile Trp Leu Ala Arg Tyr Gly Asn Ile Gln
130                 135                 140

Pro Ile Gly Lys Gln Ile Ala Thr Ala Thr Val Gly Gly Lys Ser Trp
145                 150                 155                 160

Glu Val Trp Tyr Gly Ser Thr Thr Gln Ala Gly Ala Glu Gln Arg Thr
                165                 170                 175

Tyr Ser Phe Val Ser Glu Ser Pro Ile Asn Ser Tyr Ser Gly Asp Ile
                180                 185                 190

Asn Ala Phe Phe Ser Tyr Leu Thr Gln Asn Gln Gly Phe Pro Ala Ser
                195                 200                 205

Ser Gln Tyr Leu Ile Asn Leu Gln Phe Gly Thr Glu Ala Phe Thr Gly
    210                 215                 220

Gly Pro Ala Thr Phe Thr Val Asp Asn Trp Thr Ala Ser Val Asn
225                 230                 235
```

(2) INFORMATION FOR SEQ ID NO:3:

(i) SEQUENCE CHARACTERISTICS:
       (A) LENGTH: 1198 base pairs
       (B) TYPE: nucleic acid
       (C) STRANDEDNESS: double
       (D) TOPOLOGY: linear (ii) MOLECULE TYPE: cDNA (iii) HYPOTHETICAL: NO (iv) ANTI-SENSE: NO (vi) ORIGINAL SOURCE:
       (A) ORGANISM: Aspergillus niger
       (B) STRAIN: N400
       (C) INDIVIDUAL ISOLATE: CBS120.49

(ix) FEATURE:
       (A) NAME/KEY: Coding Sequence
       (B) LOCATION: 32...1024
       (D) OTHER INFORMATION: product="Cellulase"

(xi) SEQUENCE DESCRIPTION: SEQ ID NO:3:

GAATTCGGCA CGAGATCGAG CAGTCGTAGC G ATG AAG TTT CAG AGC ACT TTG        52

-continued

```
                    Met Lys Phe Gln Ser Thr Leu
                     1               5
CTT CTT GCC GCC GCG GCT GGT TCC GCG TTG GCT GTG CCT CAT GGC TCC        100
Leu Leu Ala Ala Ala Ala Gly Ser Ala Leu Ala Val Pro His Gly Ser
         10              15                  20

GGA CAT AAG AAG AGG GCG TCT GTG TTT GAA TGG TTC GGA TCG AAC GAG        148
Gly His Lys Lys Arg Ala Ser Val Phe Glu Trp Phe Gly Ser Asn Glu
         25              30              35

TCT GGT GCT GAA TTT GGG ACC AAT ATC CCA GGC GTC TGG GGA ACC GAC        196
Ser Gly Ala Glu Phe Gly Thr Asn Ile Pro Gly Val Trp Gly Thr Asp
40              45              50                  55

TAC ATC TTC CCC GAC CCC TCG ACC ATC TCT ACG TTG ATT GGC AAG GGA        244
Tyr Ile Phe Pro Asp Pro Ser Thr Ile Ser Thr Leu Ile Gly Lys Gly
                60              65              70

ATG AAC TTC TTC CGC GTC CAG TTC ATG ATG GAG AGG TTG CTT CCT GAC        292
Met Asn Phe Phe Arg Val Gln Phe Met Met Glu Arg Leu Leu Pro Asp
             75              80              85

TCG ATG ACT GGT TCA TAC GAC GAG GAG TAT CTG GCC AAC TTG ACG ACT        340
Ser Met Thr Gly Ser Tyr Asp Glu Glu Tyr Leu Ala Asn Leu Thr Thr
         90              95              100

GTG GTG AAA GCG GTC ACG GAT GGA GGC GCG CAT GCG CTC ATC GAC CCT        388
Val Val Lys Ala Val Thr Asp Gly Gly Ala His Ala Leu Ile Asp Pro
     105             110             115

CAT AAC TAT GGC AGA TAC AAC GGG GAG ATC ATC TCC AGT ACA TCG GAT        436
His Asn Tyr Gly Arg Tyr Asn Gly Glu Ile Ile Ser Ser Thr Ser Asp
120             125             130                 135

TTC CAG ACT TTC TGG CAG AAT CTG GCG GGC CAG TAC AAA GAT AAC GAC        484
Phe Gln Thr Phe Trp Gln Asn Leu Ala Gly Gln Tyr Lys Asp Asn Asp
                140             145             150

TTG GTC ATG TTT GAT ACC AAC AAC GAA TAC TAC GAC ATG GAC CAG GAT        532
Leu Val Met Phe Asp Thr Asn Asn Glu Tyr Tyr Asp Met Asp Gln Asp
            155             160             165

CTC GTG CTG AAT CTC AAC CAA GCA GCC ATT AAC GGC ATC CGC GCT GCA        580
Leu Val Leu Asn Leu Asn Gln Ala Ala Ile Asn Gly Ile Arg Ala Ala
        170             175             180

GGT GCA AGC CAG TAC ATT TTC GTC GAA GGC AAC TCC TGG ACC GGA GCT        628
Gly Ala Ser Gln Tyr Ile Phe Val Glu Gly Asn Ser Trp Thr Gly Ala
    185             190             195

TGG ACA TGG GTC GAT GTC AAC GAT AAT ATG AAG AAT TTG ACC GAC CCA        676
Trp Thr Trp Val Asp Val Asn Asp Asn Met Lys Asn Leu Thr Asp Pro
200             205             210             215

GAA GAC AAG ATC GTC TAT GAA ATG CAC CAG TAC CTA GAC TCC GAC GGT        724
Glu Asp Lys Ile Val Tyr Glu Met His Gln Tyr Leu Asp Ser Asp Gly
                220             225             230

TCC GGC ACT TCG GAG ACC TGT GTC TCC GGG ACA ATC GGA AAG GAG CGG        772
Ser Gly Thr Ser Glu Thr Cys Val Ser Gly Thr Ile Gly Lys Glu Arg
            235             240             245

ATC ACT GAT GCT ACA CAG TGG CTC AAG GAC AAT AAG AAG GTC GGC TTC        820
Ile Thr Asp Ala Thr Gln Trp Leu Lys Asp Asn Lys Lys Val Gly Phe
        250             255             260

ATC GGC GAA TAT GCC GGG GGG TCC AAT GAT GTG TGT CGG AGT GCC GTG        868
Ile Gly Glu Tyr Ala Gly Gly Ser Asn Asp Val Cys Arg Ser Ala Val
    265             270             275

TCC GGG ATG CTA GAG TAC ATG GCG AAC AAC ACC GAC GTA TGG AAG GGT        916
Ser Gly Met Leu Glu Tyr Met Ala Asn Asn Thr Asp Val Trp Lys Gly
280             285             290             295

GCG TCG TGG TGG GCA GCC GGG CCA TGG TGG GGA GAC TAC ATT TTC AGC        964
Ala Ser Trp Trp Ala Ala Gly Pro Trp Trp Gly Asp Tyr Ile Phe Ser
                300             305             310
```

```
CTG GAG CCC CCA GAT GGA ACT GCT TAC ACG GGT ATG CTG GAT ATC CTG        1012
Leu Glu Pro Pro Asp Gly Thr Ala Tyr Thr Gly Met Leu Asp Ile Leu
        315                 320                 325

GAG ACG TAT CTC TGAGAACTGG GTGGGGTCGC AGATGCGGTG CGTCGGAGAA CTATA      1069
Glu Thr Tyr Leu
        330

CGGAGTTTCT TATCAGAGTG GACGGTGGTG GTACAGAGAG GCGTACTAGA ATGAATTAGT     1129

GGCAGCGCAC TGACTGACGT CACAAGACAT TGCTTTTTTT GTGAAAAAAA AAAAAAAAAA     1189

AAACTCGAG                                                            1198
```

(2) INFORMATION FOR SEQ ID NO:4:

(i) SEQUENCE CHARACTERISTICS:
        (A) LENGTH: 331 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:4:

```
Met Lys Phe Gln Ser Thr Leu Leu Ala Ala Ala Gly Ser Ala
1               5                   10                  15

Leu Ala Val Pro His Gly Ser Gly His Lys Lys Arg Ala Ser Val Phe
                20                  25                  30

Glu Trp Phe Gly Ser Asn Glu Ser Gly Ala Glu Phe Gly Thr Asn Ile
            35                  40                  45

Pro Gly Val Trp Gly Thr Asp Tyr Ile Phe Pro Asp Pro Ser Thr Ile
        50                  55                  60

Ser Thr Leu Ile Gly Lys Gly Met Asn Phe Phe Arg Val Gln Phe Met
65                  70                  75                  80

Met Glu Arg Leu Leu Pro Asp Ser Met Thr Gly Ser Tyr Asp Glu Glu
                85                  90                  95

Tyr Leu Ala Asn Leu Thr Thr Val Val Lys Ala Val Thr Asp Gly Gly
                100                 105                 110

Ala His Ala Leu Ile Asp Pro His Asn Tyr Gly Arg Tyr Asn Gly Glu
            115                 120                 125

Ile Ile Ser Ser Thr Ser Asp Phe Gln Thr Phe Trp Gln Asn Leu Ala
130                 135                 140

Gly Gln Tyr Lys Asp Asn Asp Leu Val Met Phe Asp Thr Asn Asn Glu
145                 150                 155                 160

Tyr Tyr Asp Met Asp Gln Asp Leu Val Leu Asn Leu Asn Gln Ala Ala
                165                 170                 175

Ile Asn Gly Ile Arg Ala Ala Gly Ala Ser Gln Tyr Ile Phe Val Glu
            180                 185                 190

Gly Asn Ser Trp Thr Gly Ala Trp Thr Trp Val Asp Val Asn Asp Asn
        195                 200                 205

Met Lys Asn Leu Thr Asp Pro Glu Asp Lys Ile Val Tyr Glu Met His
            210                 215                 220

Gln Tyr Leu Asp Ser Asp Gly Ser Gly Thr Ser Glu Thr Cys Val Ser
225                 230                 235                 240

Gly Thr Ile Gly Lys Glu Arg Ile Thr Asp Ala Thr Gln Trp Leu Lys
                245                 250                 255

Asp Asn Lys Lys Val Gly Phe Ile Gly Glu Tyr Ala Gly Gly Ser Asn
                260                 265                 270
```

-continued

```
Asp Val Cys Arg Ser Ala Val Ser Gly Met Leu Glu Tyr Met Ala Asn
        275                 280                 285

Asn Thr Asp Val Trp Lys Gly Ala Ser Trp Trp Ala Ala Gly Pro Trp
    290                 295                 300

Trp Gly Asp Tyr Ile Phe Ser Leu Glu Pro Pro Asp Gly Thr Ala Tyr
305                 310                 315                 320

Thr Gly Met Leu Asp Ile Leu Glu Thr Tyr Leu
                325                 330
```

US 6,306,635 B1

FUNGAL CELLULASES

This is a Divisional of prior application Ser. No: 08/849,751 filed Jun. 12, 1997 now U.S. Pat. No. 6,190,890.

TECHNICAL FIELD OF THE INVENTION

The present invention relates to novel enzymes. More specifically, the invention relates to novel fungal cellulases and methods of obtaining the DNA encoding them.

BACKGROUND

There is an increasing interest in glucanases in the food and feed industries. These enzymes find application for instance in the fruit juice industry for liquefaction of plant cell wall material (pending application EP 94202442.3). They may also serve as processing aids to reduce fouling of membranes. In the feed industry the role of β-glucanases in reducing the viscosity of various sorts of grains is well established. Many of the enzyme preparations used in the food and feed area are derived from Aspergillus species, usually *Aspergillus niger*. This is a safe host which produces a large variety of enzymes such as pectinases and hemicellulases with characteristics which make them suitable for applications at moderate temperatures and at neutral to acidic pH. In contrast to pectinases and hemicellulases, cellulases are usually derived from Trichoderma. Trichoderma species such as *reesei, viride* or *longibrachiatum* are good producers of cellulolytic enzymes. However, Trichoderma enzymes cannot be used everywhere due to regulatory constraints. Thus, it would be of considerable economic value to have a good source of Aspergillus enzyrries. However, up till now, it has not been possible to clone the genes encoding glucanases from *A. niger* using the traditional method involving enzyme purification, partial amino acid sequencing and isolation of the gene or cDNA for the enzyme of interest by the derived DNA sequence.

SUMMARY

The present invention provides polydeptides with cellulase activity, corresponding DNA sequences, vectors, transformed hosts and a method for the production of these polypeptides which are obtainable from *Aspergillus niger var. niger* or *Aspergillus niger var. tubigensis*.

DETAILED DESCRIPTION

Figure 1:
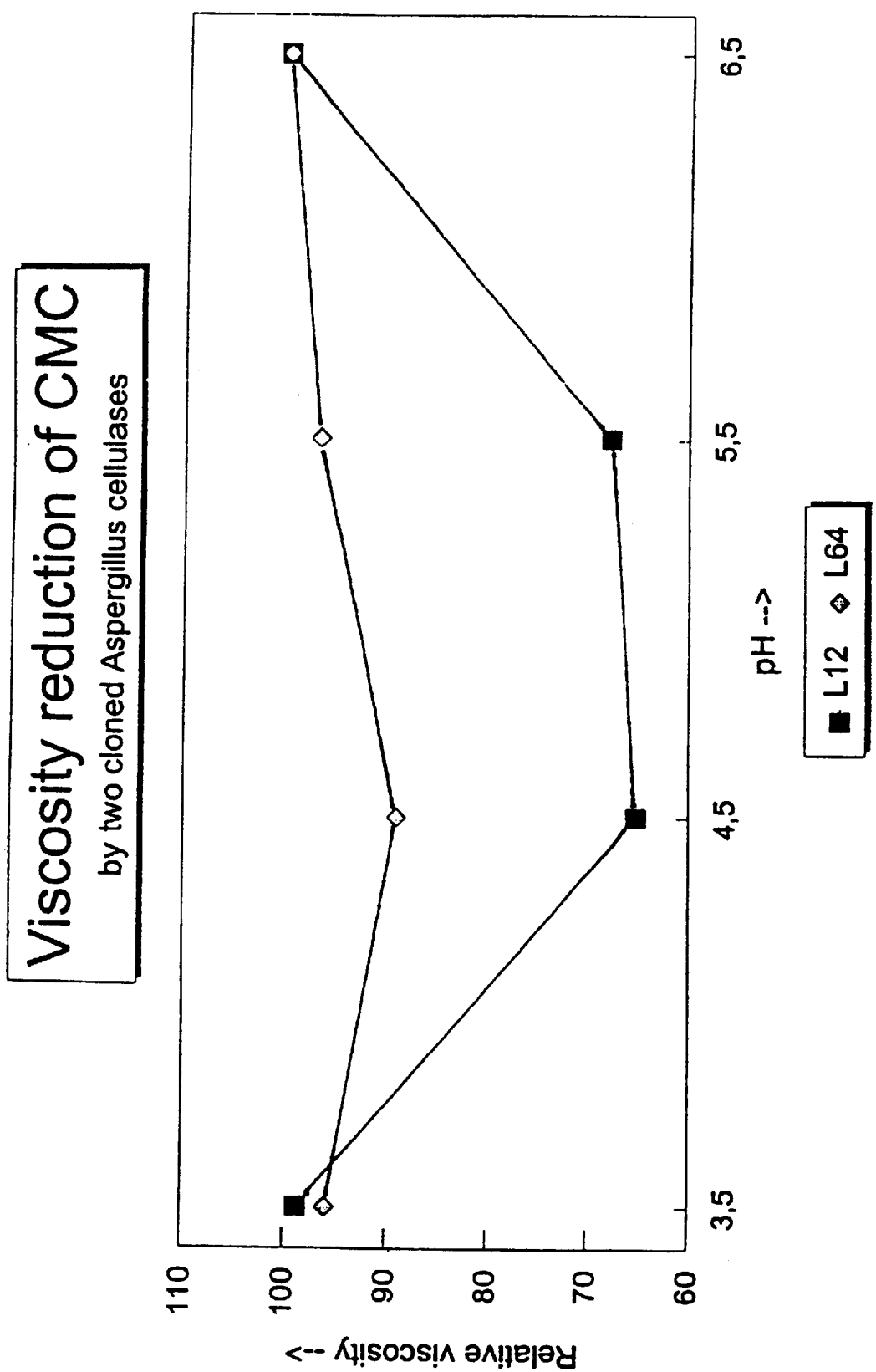
FIG. 1 shows viscosity reduction due to CMCase activity of *Aspergillus niger* cellulases.

The present invention relates to novel fungal cellulases and to methods of identifying the DNA which encodes these fungal cellulases.

In the method according to the invention, fungal cellulases are cloned by expression cloning using a cDNA library in the form of prokaryotic host cells which have been transformed with DNA which is obtainable from fungi. Screening of the host cells is performed after the cDNA has been inserted into a plasmid. The prokaryotic host cells are preferably bacterial cells, more preferably *E. coli*.

In the present context, the term 'cellulase' refers to an enzyme which degrades carboxymethyl cellulose (CMC) and/or β-1,3-glucan and/or β-1,4 glycan and/or xyloglucan.

In contrast to existing methods, the method according to the invention is quick, straightforward and efficient. Surprisingly high numbers of cellulase-positive clones are found by screening $10^2$–$10^4$ clones, rather than $10^5$–$10^6$ which is the case for existing methods (Dalbøge & Heldt-Hansen (1994) *Mol. Gen. Genet.* 243: 253–260).

Another surprising advantage of the method is that in contrast to most existing colony screening methods, there is no need to subsequently lyse bacterial colonies to release their contents, including possible gene products of interest.

Expression cloning according to the invention may be carried out in prokaryotic cells, there is no need to transfer genetic material into an eukaryotic organism anywhere during the cloning procedure.

The cDNA library is prepared from the mRNA of a fungus of interest. Examples of fungi of particular interest are those of the genus Aspergillus, more specifically *Aspergillus niger var. niger* or *A. niger var. tubigensis*.

The mRNA which is used to prepare cDNA may be constitutively present or its expression may be induced. The method according to the invention is so effective that a large percentage of colonies will produce the cellulase of interest.

The library is constructed in a vector. This vector may be any vehicle suitable for the transfer and/or expression of genetic material, including plasmid and phage vectors.

In a preferred embodiment, the library is constructed in a phage vector, preferably a ZAP™ vector or a derivative thereof, more preferably λ Uni-ZAP™ XR. The primary library which is obtained in this way is amplified using a suitable host cell, preferably *E. coli*, more preferably *E. coli* XL1 Blue MRF'.

The phages are then converted into phagemids, preferably by superinfection with a filamentous helper phage and an *E. coli* host strain, such as *E. coli* SOLR. In this way a double stranded phagemid is created. Herein, the term 'phagemid' refers to a phage genome which has been converted into a plasmid. Since all plaques are converted into phagemids prior to screening, clones showing cellulase activity with low mRNA level are not mistakenly rejected as negative for activity. Hence, it will be clear to the skilled addressee that screening in the plaque stage is superfluous.

In the identification method according to the invention, DNA encoding cellulases is cloned by screening for expression of the cellulase, i.e. cellulase activity, rather than by going through the tedious tasks of purifying the protein, amino acid sequencing and molecular cloning of the gene. One technique of expression cloning is a plate assay, wherein a cDNA library is plated on to a medium of a composition which enables screening for cellulase-positive colonies. Screening for cellulases does not require pure protein, only the availability of a suitable assay for the detection of cellulase activity. This may be a standard assay; for example, cellulase activity may be detected using an overlay containing carboxymethyl cellulose, followed by visualisation by staining with Congo Red. However, any othier kind of assay which allows the identification of DNA by expression of the protein it encodes may be used in the method according to the invention.

Alternatively, a purpose-made assay may be developed for the detection of protein activity, for example where a suitable standard assay is not available.

In addition to cellulases, other enzymes may be detected, such as amylases, arabinoxylan degrading enzymes, catalases, galactinases, lipases, oxidases, pectinases, phosphatases, proteases and xylanases. Activity of these enzymes may be detected using methods known in the art.

The present invention also provides isolated nucleic acid fragments comprising a sequence encoding a polypeptide of the invention, i.e., a cellulase obtainable from *Aspergillus niger var. niger* or *A. niger var. tubigensis*.

The nucleic acid fragments of the invention may comprise DNA or RNA, preferably DNA. Two preferred DNA fragments of the invention are those whose nucleic acid sequences are given in SEQ ID. No. 1 and 3. The nucleic acid fragments of the invention are not, however, limited to these preferred fragments. Rather, the invention also encompasses variants of SEQ ID No. 1 and 3 obtainable from *Aspergillus niger var. niger* or *Aspergillus niger var. tubigensis* encoding polypeptides having cellulase activity. For example, therefore, the invention provides degenerate variants of SEQ ID. No. 1 or 3 that encode the polypeptides of SEQ ID No. 2 or 4. Similarly, such variant nucleic acid fragments may code for variants of the polypeptides of SEQ ID. No. 2 or 4, which variant polypeptides differ from SEQ ID NO. 2 or 4 by the deletion, insertion or substitution of one or more amino acids, as long as the deletion, insertion or substitution does not abolish the cellulase activity of the polypeptide. Thus, the variant polypeptides of the invention retain some or all of the activity, typically substantially the activity, of the polypeptide of SEQ ID NO. 2 or 4.

Also, the invention provides variant isolated nucleic acid, preferably DNA, fragments having a high degree of sequence identity with the nucleic acid sequences of SEQ ID. No. 1 or 3. Thus they are typically substantially homologous to SEQ ID. NO. 1 or 3. Typically, such variant fragments have at least 90% sequence identity with SEQ ID No. 1 or 3. Similarly, such variant fragments may differ from SEQ ID No. 1 or 3 by the deletion, substitution or insertion of one or more amino acids, as long as the deletion, substitution or insertion does not abolish the cellulase activity of the encoded polypeptide. Thus, the encoded polypeptide retains some or all of the cellulase activity of the polypeptide of SEQ ID No. 2 or 4.

Variant nucleic acid fragments of the invention may be obtained from any organism, although they are preferably obtained from fungi or yeasts, more preferably fungi of the genus Aspergillus, most preferably *A. niger* or *A. tubigensis*.

The invention also provides recombinant nucleic acids, preferably DNA, comprising the nucleic acid fragments of the invention. Typically, these are in the form of recombinant nucleic acid vectors.

A vector of the invention may be of any type known in the art, and may comprise DNA or RNA, as appropriate. For example, the construct may be in linear or circular form. Plasmids are one preferred type of vector. Vectors of the invention may be cloning vectors; these are useful in multiplying the nucleic acid fragments of the invention, and in the isolation and identification of nucleic acids of the invention. Vectors of the invention may also be expression vectors; these are useful for identifying nucleic acids of the invention by expression cloning, and for producing polypeptides of the invention. The same vector can act, when appropriate, as a cloning vector and an expression vector for expression cloning, as described herein for λ phage vectors.

Those of skill in the art will be able to prepare suitable vectors of the invention starting with widely available vectors which will be modified by genetic engineering techniques known in the art, such as those described by Sambrook et al (Molecular cloning: a Laboratory Manual; 1989).

A vector according to the invention typically comprises one or more origins of replication so that it can be replicated in a host cell, such as a bacterial, yeast or fungal cell (this enables constructs to be replicated and manipulated, for example in *E. coli*, by standard techniques of molecular biology). A vector, especially an expression vector, also typically comprises at least the following elements, usually in a 5' to 3' arrangement: a promoter for directing expression of the nucleic acid sequence and optionally a regulator of the promoter, a transcription start site, a translational start codon, and a nucleic acid sequence of the invention.

The vector may also contain one or more selectable marker genes, for example one or more antibiotic resistance genes. Such marker genes allow identification of transformants. Optionally, the construct may also comprise an enhancer for the promoter. The vector may also comprise a polyadenylation signal, typically 3' to the nucleic acid encoding the functional polypeptide. The vector may also comprise a transcriptional terminator 3' to the sequence encoding the polypeptide of interest.

The vector may also comprise one or more introns or other non-coding sequences, for example 3' to the sequence encoding the polypeptide of the invention.

In a typical vector, the nucleic acid sequence of the invention is operably linked to a promoter capable of expressing the sequence. "Operably linked" refers to a juxtaposition wherein the promoter and the nucleic acid sequence encoding the polypeptide or protein are in a relationship peninitting the coding sequence to be expressed under the control of the promoter. Thus, there may be elements such as 5' non-coding sequence between the promoter and coding sequence. Such sequences can be included in the vector if they enhance or do not impair the correct control of the coding sequence by the promoter.

Any suitable promoter that is capable of directing expression of the nucleic acid encoding the polypeptide of the invention may be included in the vector. For example, the promoter may be a bacterial, eukaryotic or viral promoter. The promoter may be constitutive or inducible.

The invention also provides recombinant host cells harbouring recombinant nucleic acids of the invention, either integrated into the host cell genome or free in the cell. The host cell may be of any suitable type. For example the host cell may be a bacterial (e.g. *E. coli*), yeast (e.g. *K. lactis*), fungal (e.g. Aspergillus), animal (e.g. insect or mammalian) or plant cell. Bacterial host cells are, for example, useful in the expression cloning of DNA fragments of the invention. Bacterial and other cell types may be useful in producing polypeptides of the invention.

The recombinant nucleic acid of the invention may be introduced into the host cell by any means known in the art. For example, the host cell may be transformed or transfected by any suitable method, such as the methods disclosed by Sambrook et al (Molecular cloning: A Laboratory Manual; 1989). For example, recombinant nucleic acids comprising nucleic acid sequences according to the invention may be packaged into infectious viral particles, such as retroviral particles. The recombinant nucleic acids may also be introduced, for example, by electroporation, calcium phosphate precipitation, lipofection, biolistic methods or by contacting naked recombinant nucleic acids with the host cell.

The invention also provides polypeptides encoded by the nucleic acids of the invention. These polypeptides have cellulase activity, as defined herein. Two preferred polypeptides of the invention are those whose sequences are given in SEQ ID NO. 2 and 4. However, the invention is not limited to these sequences; rather, it encompasses all polypeptides encoded by the nucleic acid fragments of the invention. That have cellulase activity, as defined herein.

In particular, the invention provides variant polypeptides having sequences related to those of SEQ ID NO. 2 and 4. Typically, such variants have a high degree of sequence identity with SEQ ID NO. 2 or 4, for example at least 70% sequence identity, thus, they are typically substantially homologous to the polypeptides of SEQ ID NO. 2 or 4. Similarly, variant polypeptides of the invention may differ from SEQ ID NO. 2 or 4 by the deletion, insertion or substitution of one or more amino acids, as long as the deletion, insertion or substitution does not abolish the cellulase activity of the polypeptide. Thus, the variant polypeptides of the invention retain some or all of the activity, typically substantially the activity, of the polypeptide of SEQ ID NO. 2 or 4.

Polypeptides of the invention may be in isolated form. For example they may be substantially or completely isolated.

The invention also provides methods of producing polypeptides of the invention. These comprise culturing host cells of the invention under conditions that permit the expression of polypeptides of the invention from the recombinant nucleic acids of the invention; and, optionally, recovering the polypeptide thus produced.

The polypeptide may be recovered by any suitable means known in the art.

UTILITY

Cellulases according to the invention may be used, alone or in combination with other enzymes, in the food industry, e.g. for the liquefaction of plant cell material, e.g. in vegetable or fruit juice manufacturing, or as processing aids to reduce fouling of membranes.

The cellulases may also be used in the feed industry. Examples of applications are their use for the improvement of feed utilization by breaking down cell walls and for reducing the viscosity of various kind of grains.

Another application is in the textile industry for the treatment of both woven and knitted fabric, e.g. to achieve quality improvement or special effects (worn look).

Yet another application is in the detergent industry, e.g. in a detergent composition. The detergent composition may be formulated in any convenient form, such as powder, liquid, etc. The detergent composition may contain one or more other enzymes and other ingredients known in the art, such as builders, bleaching agents, perfumes etc.

The cellulases according to the invention may also be used in the pulp and paper industry for biopulping and biobleaching.

EXPERIMENTAL

Standard recombinant DNA technology such as bacterial growth, DNA isolation, hybridisation, restriction enzyme digestion and DNA sequencing are according to Sambrook et al. (1989): Molecular cloning, a laboratory manual, Cold Spring Harbor Laboratory Press, New York.).

EXAMPLES

Example I
Construction of *Aspergillus niger* cDNA Expression Library in *E. coli*.

Example I.1.
Induction and Isolation of mRNA

*A. niger* N400 cultures were grown for 69 and 81 h respectively, as described in EP-A-0 463 706 without yeast extract and with 2% crude wheat arabinoxylan fraction instead of oat spelt xylan, after which the mycelium was harvested by filtration and then washed with sterile saline. The mycelium was subsequently frozen in liquid nitrogen after which it was powdered using a Microdismembrator (Braun). Total RNA was isolated from mycelial powder in accordance with the guanidium thiocyanate/CsCl protocol described in Sambrook et al. (1989), except that the RNA was centrifuged twice using a CsCl gradient. Poly $A^+$ mRNA was isolated from 5 mg of total RNA by oligo (dT)-cellulose chromatography (Aviv and Leder, 1972, Sambrook et al., 1989) with the following modifications: SDS is omitted from all solutions and the loading buffer was supplemented with 9% (v/v) dimethylsulfoxide.

Example I.2
Construction of the cDNA Library.

cDNA was synthesized from 7 μg poly $A^+$ mRNA and ligated into bacteriophage lambda λ Uni-ZAP XR using the ZAP™-cDNA synthesis kit (Stratagene) according to the manufacturer's instructions. After ligation of the cDNA into Uni-ZAP XR vector-arms, the phage DNA was packaged using Packagene™ extracts (Promega) according to the manufacturers instructions. Ligation of 120 ng cDNA in 1.2 μg vector arms and subsequent packaging of the reaction mixture resulted in a primary library consisting of $3.5 \times 10^4$ recombinant phages. This primary library was amplified using *E.coli* XL1-Blue MRF', titrated and stored at 4° C.

Example I.3
Conversion of Phages into Phagemids.

Phages were propagated by plating them in NZYCM topagarose containing 0.7% agarose on 85 mm diameter NZYCM (1.5% agar) plates as described by Maniatis et al. (Maniatis et al. (1982): Molecular cloning, a laboratory manual, Cold Spring Harbor Laboratory, Cold Spring Harbor, N.Y. pp 64) using *E. coli* BB4 as plating bacteria. After overnight incubation at 37° C. confluent plates were obtained from which the phages were eluted by adding 5 ml SM buffer and storing the plate for 2 hrs at 4° C. with intermittent shaking. After collection of the supernatant, the bacteria were removed from the solution by centrifugation at 4.000×g at 4° C. for 10 min. To the supernatant, 0.3% chloroform was added and the number of plaque forming units (pfu) was determined. The phage stock contained approximately $10^{10}$ pfu/ml.

The recombinant Uni-ZAP XR clones containing *A. niger* cDNA were converted to Bluescript phagemids using superinfection with the filamentous helper phage EXASSIST™ and *E. coli* SOLR strain which are included in the cDNA synthesis kit from Stratagene, according to the manufacturer's instructions. For long term storage a glycerol stock containing about 100 colonies per μl of suspension was stored at −80° C.

Example II
Screening of a Plasmid cDNA Library for Cellulase-producing Colonies.

The screening procedure was modified from Wood et al. (Methods in Enzymology 160, 59–74). Plates contained 20 ml 2×TY, 0.2% CMC (Sigma C-4888), 1.5% agar and 100 μg ampicillin per ml. Cells were plated in an overlay of 5 ml containing about 200 colonies per plate. The overlay was kept at 50° C. and contains 2×TY, 0.2% CMC, 0.75% agar and 100 μg ampicillin per ml. Plates were covered with 5 ml 0.5% agarose, 0.2% CMC and 100 μg ampicillin per ml kept at 50° C. after drying, the plates were incubated for 48 hrs at 37° C. Next, 5 ml 0.1% Congo Red (Aldrich no C8, 445.3) was poured on the plates. After staining for 1–2 hrs plates were destained with 5 ml 5M NaCl for 0.5–1 hrs.

About 12.000 colonies from *A. niger* cDNA library (Example I) were plated. Screening on CMC resulted in 89 colonies giving a halo after staining with Congo Red. Colonies were subdivided in 3 classes with a large, intermediate and a small halo. From each class 3 colonies were grown up, plasmicis isolated and cDNAs sequenced. All contained a full length cDNA copy. The plasmids fell into two separate classes. From each class a colony was deposited at the CBS, Baarn, the Netherlands. A colony giving a small halo was deposited on Aug. 3, 1995 and designated CBS 589.95 (cDNA 12). A colony giving a large halo was deposited on Sep. 21, 1995 and designated CBS 662.95 (cDNA 64). The DNA sequences of the inserts are presented in SEQ ID No. 1 and 3, together with the amino acid sequences encoded by them.

The above shows that DNA fragments encoding fungal cellulases can be identified by expression cloning in prokaryotic host cells using a plasmid vector. The following examples illustrate how cDNAs thus identified can be used to construct strains overproducing cellulases.

Example III

Overexpression of Fungal Cellulases in Aspergillus.

Overexpression of cellulases may be obtained in any suitable manner, e.g., in a similar way as has been described for phytase in EP-A-0 420 358 or xylanase in EP-A0 463 706. The following elements from these applications are relevant for overexpression.

The *A. niger* amyloglucosidase (AG) promoter which ensures high level expression of cellulase cDNAs.

A terminator for transcription can be taken from the xylanase or phytase genes. A sequence about 400–500 bp is sufficient for termination.

The *A. nidulans* AmdS marker from pGW 325 (Wernars K 1986, Thesis, Agricultural University of Wageningen, the Netherlands).

*A. niger* strain CBS 513.88 is a suitable receptor strain.

The connection between the AG promoter and the cellulase cDNAs can be made using a fusion PCR (polymerase chain reaction) as described. Typically, fusion oligonucleotides are about 36 bases long and overlap both sequences at the start codon for transcription. The fusion PCR gives rise to a DNA fragment which can be cleaved using restriction enzymes and subsequently ligated in an *E. coli* vector. Similarly, a fusion experiment can be performed fusing the stop codon for translation of the cellulase cDNAs to the terminators of xylanase or phytase. Sequences for these terminators have been published in EP-A0 420 358 and EP-A0 463 706.

The fragments from the fusion PCR experiments are sequenced to check for is possible errors and subsequently the DNA fragment are ligated in a plasmid containing cellulase cDNA under control of the AG promoter and a suitable terminator. The AmdS marker can be added to this construct at any stage. All construction work is performed in *E. coli*.

The DNA fragment is transformed to *A. niger* CBS 413.88 as described in Tilburn et al. (1983) Gene 26:205–221 and Kelly & Hynes (1985) EMBO J 4:475–479, modified as described in EP-A0 463 706.

Example IV

Overexpression of Fungal Cellulases in *K. lactis*

Example IV.1

Construction of Expression Vectors

Starting vector pGBHSA20 was deposited at the CBS, Baarn, the Netherlands, on Oct. 3, 1996, and designated CBS 997.96. This vector contains the promoter and terminator sequence of the lactase gene (lac4) of *K. lactis* and a G418 selection marker. The present cDNA insert encoding HSA (human serum albumin) was replaced by cellulase encoding cDNA12 and cDNA64 from *A. niger*. For cloning the *A. niger* cDNA12, a 3' XhoI site was present. The 5' HindIII site was created by subcloning a KpnI/EcoRI fragment containing the full length cDNA12, in the corresponding sites of vector pMTL22P. Digestion with HindIII, adjacent to the EcoRI site of the cDNA, and a subsequent partial digestion with XhoI (cDNA12 contains an internal XhoI site) released a HindIII/XhoI fragment which was cloned in the unique HindIII/XhoI sites of pGBHSA20. The resulting construct, in which the HSA encoding cDNA was replaced by cDNA12, was named pCVlac12. The same cloning strategy was followed for cDNA64, resulting in expression vector pCVlac64.

Example IV.2

Transformation of *K. lactis*

Prior to transformation vectors pCVlac12 and pCVlac64 were linearized with HpaI having a unique site in the lactase promoter which is required for homologous integration. *K. lactis* strain CBS 2359 was transformed with 15 μg vector DNA using the LiCl method as described by Ito et al. (1983) J. Bact. 153: 163–168. Transformants were selected on YePD plates (10 g/l yeast extract, 20 g/l Bacto-peptone, 20 g/l glucose, 20 g/l Bacto-agar) containing 50 μg/ml G418.

Example IV.3

Screening for Cellulase Producing *K. lactis* Transformants

*K. lactis* transformants were screened for expression of the cellulases 12 and 64 in an enzyme assay using Cellazyme C tablets containing AZCL-hemicellulose colour complex (Megazyme, Australia). Cellulases release a blue AZCL compound which can be quantified by measuring the absorbance at 590 nm.

To determine the cellulase activity in culture filtrate transformants were grown in YePD at 30° C., 200 rpm, overnight. Next day culture fluid was harvested by pelleting the cells by centrifugation. Cellulase activity in the supernatant was variable for independent transformants and cDNA64 containing transformants showed very low levels of enzyme activity compared to the cDNA12 transformants.

Expression of the cellulase cDNAs was enhanced when transformants were grown on lactose instead of glucose.

Example IV.4

Mass Production of Cellulase

*K. lactis* transformants containing the pCVlac12 or pCVlac64 construct and with highest cellulase activity as determined in the above mentioned assays, were grown in 1 liter of YeP with 2% lactose, at 30° C., 200 rpm during two days. Subsequently cells were pelleted by centrifugation and the supernatant was harvested for further characterization of enzyme activities, as described before.

Example V
Characterisation of Cloned Cellulases from Aspergillus

Example V.1
Determination of Enzyme Activity

The activity of the products from pCVlac 12 (L12) and pCVlac64 (L64) towards CMC, xyloglucan and β-glucan was determined by treating 250 μg of the substrate in 200 μL of a 50 mM NaOAc buffer pH 5 containing 0.01% (w/v) NaN$_3$ for 1 h at 40° C. The release of reducing end groups was measured according to the method of Nelson-Somogyi et al. (1952) J. Biol. Chem. 195, 19–23.

|     | CMC | Xyloglucan | β-glucan |
| --- | --- | --- | --- |
| L12 | 600 | 29 | 1923 |
| L64 | 458 | 57 | 729 |

Example V.2
Determination of pH Optimum

The pH optimum of L12 and L64 was determined using viscosity reduction.

Sample Preparation

Culture filtrate from *K.lactis* CBS 2359 containing (pCVlac12)T10 and *K.lactis* CBS 2359 containing (pVClac64)T41. Samples were concentrated by ultrafiltration prior to use.

Substrates Used

Carboxymethylcellulose ([CMC] Sigma), β-glucan from barley ([βGluc] Megazyme)

Viscosimetric Method Using a "Viscorobot"

Solutions (0.4% CMC and 0.75% β-gluc) of the substrate were made in buffers of different pH. The solutions (20 ml and up to 7 at the same time) were placed in a temperature controlled Gilson sample changer Model 222 specially programmed for this task. The substrate solutions were mixed with the sample (L12 or L64). Buffer was used as blank. At regular time intervals samples wvere withdrawn from the mixture at constant speed, using a Gilson Dilutor 401 controlled by the sample changer. On withdrawal the sample was forced through a piece of cappilair tubing, thus creating an underpressure in the system, which was free of any air. Pressure difference were proportional to viscosity of the sample. Pressure differences were registered by a pressure transducer. Signals are send to an integrator which collects the data. Data is send to a computer linked to the integrator. Viscosity reduction was plotted against time using a home made computerprogram. Relative viscosity after a fixed time interval was plotted against the pH of the solutions used.

Figure 2:
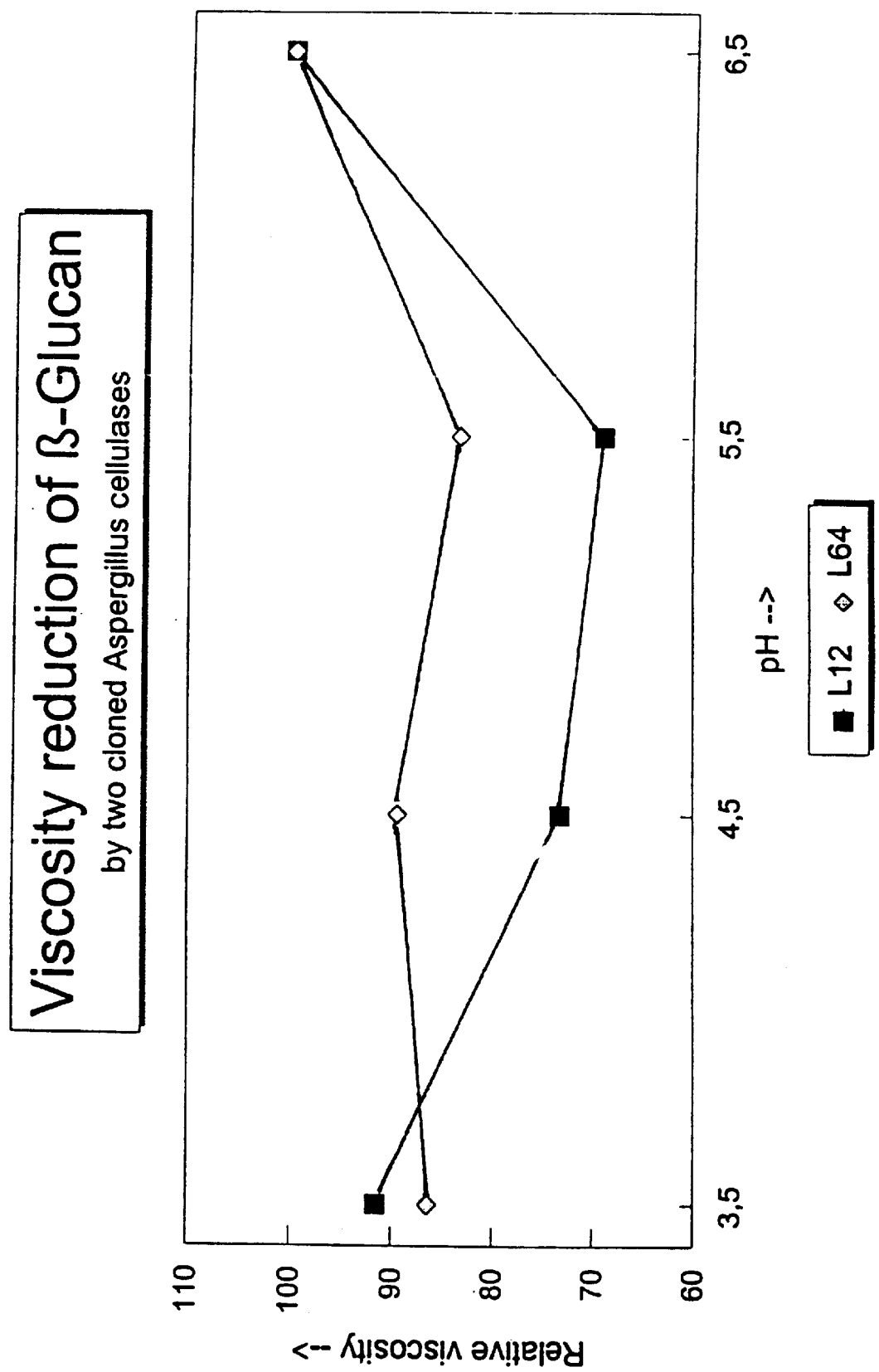
FIG. 2 shows viscosity reduction due to β-glucanase activity of *Aspergillus niger* cellulases.

FIGS. 1 and 2 show the results obtained with CMC and β-glucan. As can be seen from the figures, the CMCase pH optimum of both L12 and L64 is about pH 3.5. As can be seen from the FIG. 2, β-glucanase of both L12 and L64 is about pH 5.5

Example VI
Small Scale Cloudy Apple Juice Production.

After removing the peel and core, apple were homogenized in a Braun kitchen machine (MX32, Frankfurt, Germany; 5 mm blade). One g of apple was incubated (40° C.; 150 rpm) with 3 mL of a 200 mM NaOAc buffer (pH 4) containing 0.01% (w/v) NaN$_3$, 1% (w/v) ascorbic acid, 50 mU pectin lyase and an amount of cellulase L12 preparation which was equivalent to 29 mU CMCase activity. After 24 h, a cloudy juice was obtained. This cloud remained stable for several months.

---

What is claimed is:

1. An isolated nucleic acid fragment comprising
   (a) a sequence encoding a polypeptide having carboxymethyl cellulase (CMCase), endoglucanase, and β-glucanase activity and being indigenous to *Aspergillus niger var. niger* or *Aspergillus niger var. tubigensis;*
   (b) a sequence encoding a polypeptide having the amino acid sequence SEQ ID NO:2 or SEQ ID NO:4 or a variant thereof that differs by an addition, insertion or deletion of one or more amino acids, and which still has CMCase, endoglucanase and β-glucanase activity; wherein said variant has an amino acid sequence that has at least 70% sequence identity to the polypeptides of SEQ. ID. NO:2 or SEQ. ID. NO:4; or
   (c) a sequence shown in SEQ ID NO:1 or 3, or sequence having at least 90% sequence identity to the sequence shown in SEQ ID NO:1 or 3 and encoding a peptide having CMCase, endoglucanase, and β-glucanase activity.

2. An isolated nucleic acid fragment encoding a polypeptide having carboxymethyl cellulase (CMCase), endoglucanase and β-glucanase activity and comprising the nucleic acid sequence shown in SEQ ID NO:1 or 3, or a nucleic acid sequence having at least 90% sequence identity to the sequence shown in SEQ ID NO:1 or 3.

3. A recombinant nucleic acid molecule comprising a nucleic acid fragment as defined in claim 1.

4. A recombinant nucleic acid molecule according to claim 3, wherein the nucleic acid fragment is operably linked to nucleotide sequences capable of regulating expression in a host cell.

5. A host cell harboring a recombinant nucleic acid according to claim 4.

6. A host cell according to claim 5, which is selected from the group consisting of yeast, bacteria and fungi.

7. A method for producing a polypeptide having carboxymethyl cellulase (CMCase), endoglucanase and β-glucanase activity, which method comprises culturing a host cell as defined in claim 5 under conditions that permit the production of the polypeptide; and recovering the polypeptide thus produced.

8. A recombinant nucleic acid molecule comprising a nucleic acid fragment according to claim 2.

9. The nucleic acid fragment of claim 1 which encodes a polypeptide having CMCase, endoglucanase and β-glucanase activity which peptide is encoded by SEQ. ID. NO:1 or SEQ. ID. NO:3.

10. A recombinant nucleic acid molecule comprising a nucleic acid fragment as defined in claim 9.

11. A recombinant nucleic acid molecule according to claim 10 wherein the nucleic acid fragment is operably linked to nucleotide sequences capable of regulating expression in a host cell.

12. A host cell harboring a recombinant nucleic acid according to claim 11.

13. A method for producing a polypeptide having CMCase, endoglucanase and β-glucanase activity which method comprises culturing a host cell as defined in claim 12 under conditions that permit production of the polypeptide and optionally recovering the polypeptide thus produced.

14. A recombinant nucleic acid molecule according to claim 8, wherein the nucleic acid fragment is operably linked to nucleotide sequences capable of regulating expression in a host cell.

15. A host cell harboring a recombinant nucleic acid according to claim 14.

16. A method for producing a polypeptide having CMCase, endoglucanase and β-glucanase activity which method comprises culturing a host cell as defined in claim 15 under conditions that permit production of the polypeptide and optionally recovering the polypeptide thus produced.

* * * * *